(12) United States Patent
Hawkins et al.

(10) Patent No.: US 7,035,689 B1
(45) Date of Patent: Apr. 25, 2006

(54) CONNECTOR AND RETENTION MECHANISM FOR AN IMPLANTABLE MEDICAL DEVICE

(75) Inventors: Rodney J. Hawkins, Saugus, CA (US); Edward G. Rourke, Topanga, CA (US)

(73) Assignee: Pacesetter, Inc., Sylmar, CA (US)

( * ) Notice: Subject to any disclaimer, the term of this patent is extended or adjusted under 35 U.S.C. 154(b) by 579 days.

(21) Appl. No.: 10/270,757

(22) Filed: Oct. 14, 2002

(51) Int. Cl.
*A61N 1/375* (2006.01)

(52) U.S. Cl. .......................................... 607/37; 439/909
(58) Field of Classification Search ................. 607/37, 607/38, 127; 439/909, 325
See application file for complete search history.

(56) References Cited

U.S. PATENT DOCUMENTS

| | | | | |
|---|---|---|---|---|
| 3,158,702 A | * | 11/1964 | Vanderbilt ................. 200/51 R |
| 4,490,003 A | * | 12/1984 | Robinson ..................... 439/325 |
| 5,070,605 A | | 12/1991 | Daglow et al. ................ 29/842 |
| 5,275,620 A | | 1/1994 | Darby et al. ..................... 607/1 |
| 5,300,108 A | | 4/1994 | Rebell et al. ................. 607/127 |
| 5,324,311 A | * | 6/1994 | Acken ........................... 607/37 |
| 5,354,326 A | | 10/1994 | Comben et al. ............. 607/115 |
| 5,509,928 A | | 4/1996 | Acken ........................... 607/37 |
| 5,514,172 A | | 5/1996 | Mueller ........................ 607/122 |
| 5,514,173 A | | 5/1996 | Rebell et al. ................. 607/126 |
| 5,545,188 A | * | 8/1996 | Bradshaw et al. ............. 607/37 |
| 5,730,628 A | | 3/1998 | Hawkins ...................... 439/843 |
| 5,951,595 A | | 9/1999 | Moberg et al. ................ 607/37 |
| 6,029,089 A | | 2/2000 | Hawkins et al. ............... 607/37 |
| 6,183,305 B1 | | 2/2001 | Doan et al. .................. 439/668 |
| 6,498,952 B1 | * | 12/2002 | Imani et al. ................... 607/37 |
| 6,907,292 B1 | * | 6/2005 | Hill ............................... 607/37 |

* cited by examiner

*Primary Examiner*—Kennedy Schaetzle
*Assistant Examiner*—Jessica L. Reidel (57) ABSTRACT

A connector system for use with a sealed implantable medical device has a lead receiving channel with an open end for slidably receiving a connecting lead tip pin of an electrical lead and includes an electrically conductive connector body and a tip assembly coaxial with the connector body mounted on the proximal end thereof for slidably engageably receiving the lead tip pin. The tip assembly includes an electrically conductive retention mechanism for achieving and maintaining electrical continuity with the lead tip pin and for firmly engaging the lead tip pin as it is inserted into the lead receiving channel. The retention mechanism includes a tubular carrier coaxial with the connector body, a plurality of bearing members rotatably mounted on the tubular carrier engageable with the lead tip pin, and a resilient member biasing the bearing members into engagement with the lead tip pin.

15 Claims, 7 Drawing Sheets

CONNECTOR AND RETENTION MECHANISM FOR AN IMPLANTABLE MEDICAL DEVICE

FIELD OF THE INVENTION

The present invention relates generally to an electrical connector system for use with an implantable medical device such as a pacemaker for connecting an implantable electrical lead to the electrical circuits contained within a hermetically sealed housing of the medical device. More particularly, the invention relates to an electrical connector which requires no external tool to activate, allows immediate electrical contact upon lead insertion, minimizes lead insertion force, and accepts variations in lead pin diameters while maintaining familiar feel.

BACKGROUND OF THE INVENTION

While the present invention will be described in a specific manner as being applicable to a pacemaker, it will be understood that the invention is applicable to any other type of implantable medical device intended to stimulate body tissue.

Modern pacemakers monitor the activity of a heart and provide a stimulation pulse in the absence of normal heart activity. Advantageously, such devices are relatively small, light-weight and implantable. In order to sense and stimulate the heart, however, such pacemakers must be used with a pacemaker lead, an electrical conductor that carries electrical signals between the heart and the pacemaker. Advantageously, the pacemaker lead can be inserted into the heart transvenously through a relatively simple and well-known surgical procedure. Disadvantageously, one end of the lead (designated herein as the "connecting end") must be electrically and mechanically secured to the pacemaker in a way that provides for a long-term safe and secure, yet detachable connection. Those skilled in the pacemaker art have long sought for a simple, yet reliable and safe, technique for making this detachable electrical and mechanical connection between the pacemaker device and the connecting end of the pacemaker lead.

Figure 1:
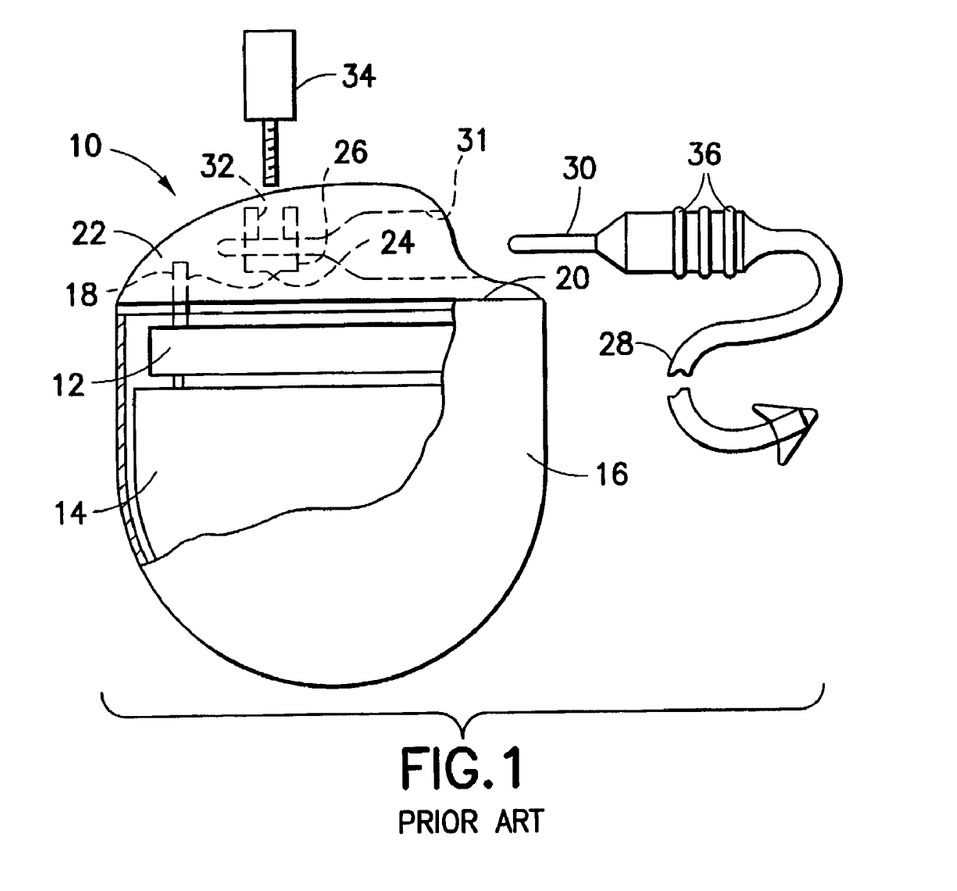
FIG. 1 is an exploded perspective view of a known implantable medical device, illustrating a sealed pacemaker housing and its associated cast epoxy connector top, and an associated lead ready for insertion into a receiving channel of the connector.

In order to appreciate the advantages of the present invention, it will help first to have a basic understanding of the manner in which the mechanical and electrical connection functions are carried out in known pacemakers. The main components associated with the connection function of such known pacemakers are shown diagrammatically in FIG. 1. A pacemaker 10 electrically includes a battery 14 that powers electrical circuits 12. The pacemaker electrical circuits 12 and battery 14 are mechanically enclosed and hermetically sealed in a suitable housing 16. Typically, this housing or case 16 is shaped to include a flat side or platform 20 to which a suitable epoxy connector 22 can be bonded. At least one feedthrough terminal 18, in electrical contact with the electrical circuits 12, passes through the case or housing 16 and protrudes beyond the platform 20. This feedthrough terminal 18 is electrically isolated from the case 16. A platinum wire 24, or other suitable conductive element, connects the terminal 18 to a conductive connector block 26 that is fitted within the connector 22. A pacemaker lead 28, having a proximal electrode 30, connects to the pacemaker electrical circuits by inserting the proximal electrode 30 into a receiving channel 31 of the connector 22 until the electrode 30 is in contact with the connector block 26. A set screw 32 is then securely tightened using a torque wrench 34 to firmly hold the electrode 30 in both mechanical and electrical connection with the connector block 26. A septum, not shown but having the construction generally described in commonly assigned U.S. Pat. No. 5,509,928 issued Apr. 23, 1996 to Acken, is typically placed over the set screw 32 in order to prevent body fluids from seeping through the set screw hole. Further, sealing ribs or ridges 36 on the connecting end of the pacemaker lead are designed to tightly engage the inside edges of the receiving channel 31 in order to prevent any body fluids from entering into the receiving channel 31 once the connecting end of the lead has been inserted into the connector 22.

While the descriptions presented in the prior art vary greatly relative to, for example, different types of locking mechanisms for performing the mechanical connection function, or different types of arrangements for performing the electrical feedthrough function, including the use of bipolar or multiple pacemaker leads, all such systems include the use of a premolded or cast connector 22 that is bonded to a sealed pacemaker housing 16 in which the electrical circuits are located.

Typically, prior art connectors 22 are cast in place from epoxy to the platform or header 20 of the pacemaker, or a premolded connector is bonded to the platform 20 using a suitable sealing and bonding agent. Further, once the electrical connection is made from the terminal post 18 to the connector block 26, and the connector is attached to the housing, all remaining voids within the connector 22, not including the receiving channel 31 into which the proximal end of the pacemaker lead 28 is to be inserted, must be filled with a suitable filler material, such as a two-component epoxy or silicone rubber.

In summary, then, of the foregoing narrative, it can be said that pacemakers and other implantable devices such as cardiac defibrillators require a method of passing electrical signals between the device and the heart. To transmit signals from the device to the heart, implantable leads are used which make electrical contact with the device through the connector top ring and tip contacts. The signals are then transmitted from the device to the heart via the implantable leads. To ensure an uninterrupted electrical path between the device and the heart, a strong reliable mating between each implantable lead and the connector contacts of the device is necessary. It is also desirable to secure the leads in place once they are inserted into the device. To achieve these connector conditions, external calibrated torque wrenches are typically used to secure the leads in place by means of setscrews or compression of seals. The use of external tools for achieving connector conditions has created reliability problems such as cored septum, stripped wrench and hex and the like. Further, time is required to ensure electrical contact while the tool is being used.

There are numerous patents which are generally illustrative of the state of the art relating to electrical connector systems used with implantable medical devices. For example, U.S. Pat. No. 5,951,595 issued to Moberg et al. discloses a connector assembly which employs an actuator mechanism for fixing and sealing electrical leads inserted into lead receptacles within the connector assembly without the use of setscrews. Typical of constructions of connector systems operable to frictionally engage the connector pin of an implantable lead are U.S. Pat. No. 5,070,605 to Daglow et al.; U.S. Pat. No. 5,275,620 to Darby et al.; U.S. Pat. No. 5,514,172 to Mueller; and U.S. Pat. No. 6,029,089 to Hawkins et al. U.S. Pat. Nos. 5,300,108 and 5,514,173 to Rebell et al. disclose active fixation leads which are extended and retracted by means of a compound screw which employs ball bearings for its operation. U.S. Pat. No.

5,354,326 to Comben et al. discloses a connector for establishing an external connection with multiple conductor implantable leads utilizing a unique twist lock design. U.S. Pat. No. 5,730,628 to Hawkins discloses a multi-contact connector for an implantable medical device using a plurality of flat spring contacts for mating electrical engagement with the electrical lead. U.S. Pat. No. 6,183,305 to Doan et al. discloses a connector assembly which employs a bayonet type interlocking construction for removably securing a connector pin of an electrical lead.

It was with knowledge of the foregoing state of the technology that the present invention has been conceived and is now reduced to practice.

SUMMARY

A connector system for use with a sealed implantable medical device has a lead receiving channel with an open end for slidably receiving a connecting lead tip pin of an electrical lead and includes an electrically conductive connector body and a tip assembly coaxial with the connector body mounted on the proximal end thereof for slidably and engageably receiving the lead tip pin. The tip assembly includes an electrically conductive retention mechanism for achieving and maintaining electrical continuity with the lead tip pin and for more firmly engaging the lead tip pin with ever increasing insertion thereof into the lead receiving channel. The retention mechanism includes a tubular carrier coaxial with the connector body, a plurality of bearing members rotatably mounted on the tubular carrier engageable with the lead tip pin, and a resilient member biasing the bearing members into engagement with the lead tip pin.

Components in one embodiment include a metal housing with a built in helical spring, a tubular carrier, ball bearings, and end helical spring, and an end cap. A feature of the metal housing is the inclusion of a helical spring. The metal housing also has an angled ramp to allow the ball bearings to roll. Within the metal housing is mounted the tubular carrier which is formed with several cavities to hold the ball bearings in place. Three ball bearings are assembled in the tubular carrier in one illustrative embodiment. More ball bearings can be included as long as they are evenly spaced. The tubular carrier is preferably made out of plastic and can be either machined or molded. Next to the metal housing is positioned an end helical spring. A small rib on the tubular carrier separates the end helical spring and the metal housing. Closing the system is an end cap, which encapsulates the end helical spring, the metal housing, and the tubular carrier. The end cap is press fitted onto the metal housing creating a slight pre load on the end helical spring.

In its free state, prior to any lead insertion, the tubular carrier is pushed back against the metal housing by a slight pre-compression of the end helical spring. This pre load of the spring is achieved when the end cap is snapped in place. At this point the tubular carrier is resting against the metal housing by its rib feature. The ball bearings are positioned at the bottom of the ramp and the built in helical spring (referred as the first helical spring) in the metal housing is fully relaxed (free state). The ball bearings are always in contact with the ramp due to the force provided by the end helical spring.

When the lead is inserted, the tip pin contacts the ball bearings. As the lead is pushed, the tip pin pushes the ball bearings up the ramp until it can roll under the balls. As the lead is further pushed, the ball bearings now roll further up the ramp. This rolling action is allowed by the compression to the ball bearings by the ramp and the lead tip pin. At the same time the ball bearings are rolling up the ramp, the tubular carrier is moving towards the end helical spring, further compressing such spring.

Once the lead is fully inserted, the translation of the tubular carrier creates a small gap between the tubular carrier rib and the metal housing. This same size gap is created between the tubular carrier and the inner wall of the metal housing. The ball bearings have rolled up the ramp and now are being compressed by the lead and the ramp. The end helical spring is compressed and applying a constant force back onto the tubular carrier. This force keeps the balls pushed back against the ramp maintaining a constant load and contact point. This contact between the ball bearings and the ramp is the source for electrical continuity in the mechanism.

To remove the lead, it is necessary to overcome the forces the ball bearings exert on the lead. These forces are the normal force and the friction force. Thus, as the lead is being pulled, the ball bearings start rolling down the ramp wedging themselves tighter and tighter between the lead and the ramp. When the ball bearings cannot move any farther, the extraction force exerted on the lead pulls back on the tubular carrier compressing the first helical spring. The first helical spring deflects until the tubular carrier hits the inner wall of the metal housing. The force required to deflect the first helical spring is the lead extraction force.

At this point, the tubular carrier cannot move any further. The first helical spring is compressed. This compression releases some of the load being exerted on the balls through the ramp. This reduces the normal load between the balls and the lead tip pin. As the lead pull out force increases, it becomes greater than the friction force and the lead tip pin starts to slide under the balls. This allows the removal of the lead from the system.

Once the lead is removed, the first helical spring relaxes back to its original free state resetting the system for the next lead insertion.

A design variation to the mechanism would be to substitute the helical springs with other types of springs. For instance, the first helical spring could be interchanged with an "S" shape spring. In addition the end helical spring could be replaced with a variety of options such as a curved washer, a wave washer, or one or more Belleville washers.

Other features, advantages, and benefits will become apparent in the following description taken in conjunction with the following drawings. It is to be understood that the foregoing general description and the following detailed description are exemplary and explanatory but are not to be restrictive. The accompanying drawings which are incorporated in and constitute a part of this invention, illustrate embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 2:
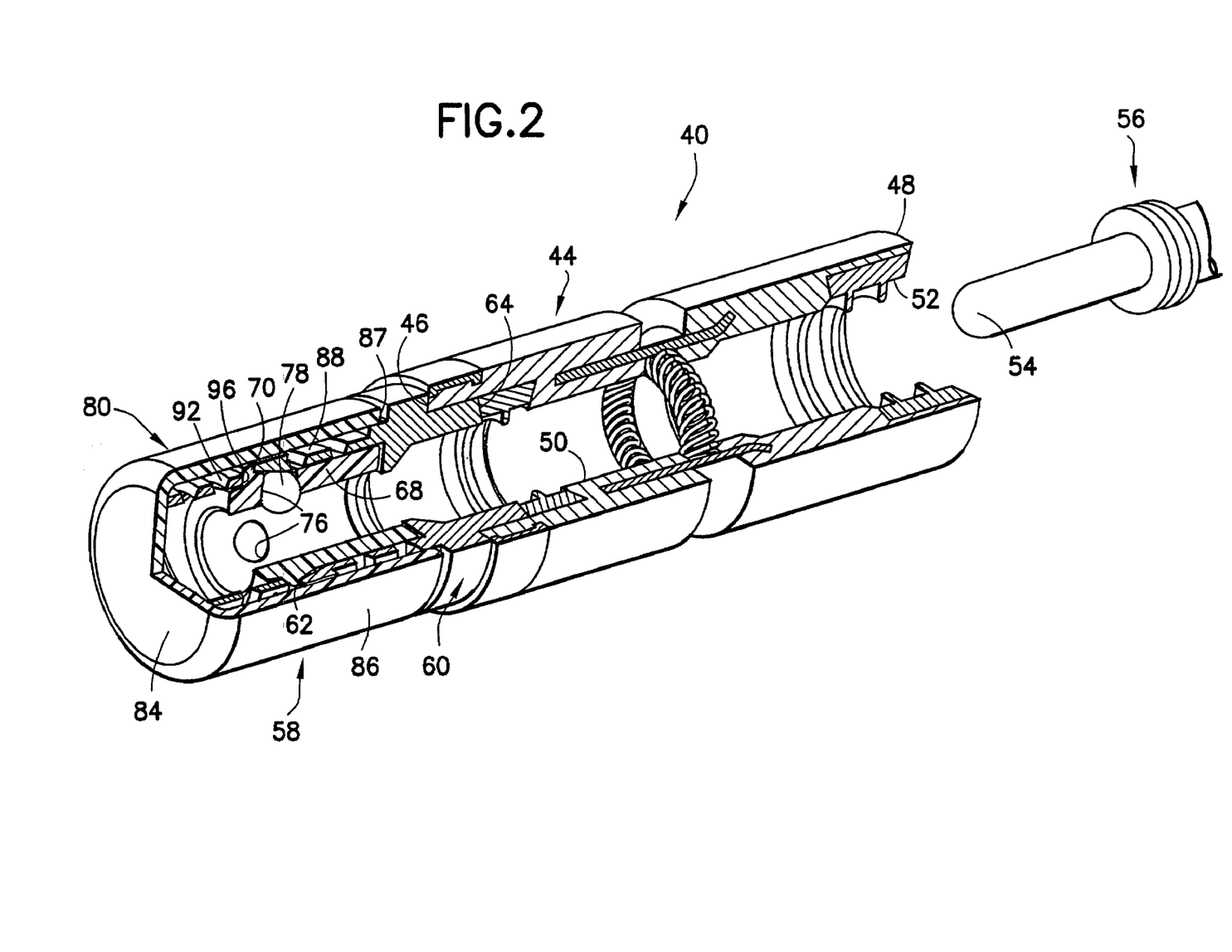
FIG. 2 is a perspective view of a connector system embodying the present invention for an implantable medical device.

Turn now to the drawings and, initially to FIG. 2 which generally illustrates a perspective view of a connector system 40 for a sealed implantable medical device such as a cardiac stimulation device, possibly in the form of the pacemaker 16. Although the present invention will be described with reference to the embodiments shown in the drawings, it should be understood that the present invention can be embodied in many alternate forms or embodiments. In addition, any suitable size, shape or type of elements or materials may be used.

Figure 3:
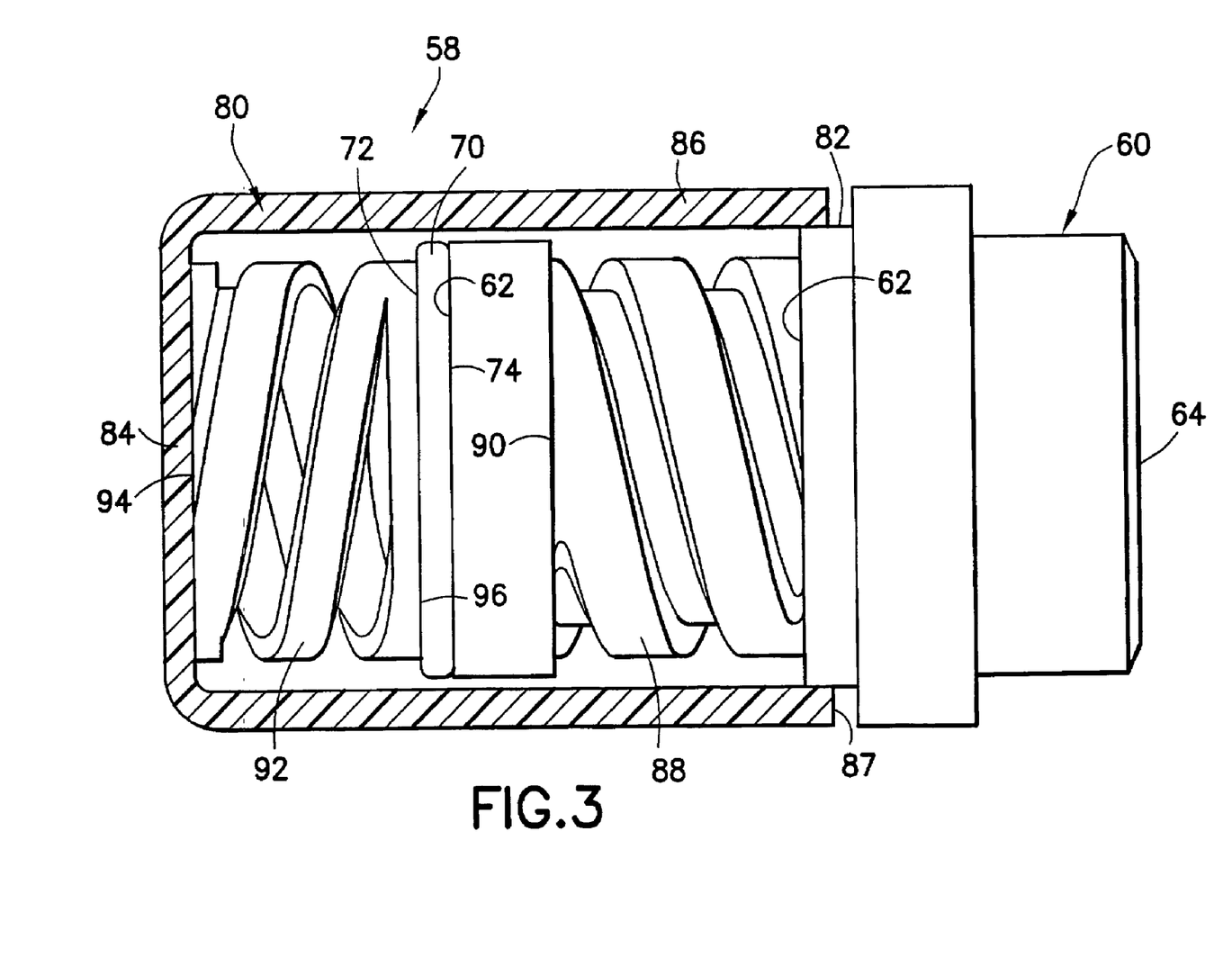
FIG. 3 is a side elevation view, certain parts being shown in section, of a part of the connector system illustrated in FIG. 2.
Figure 4:
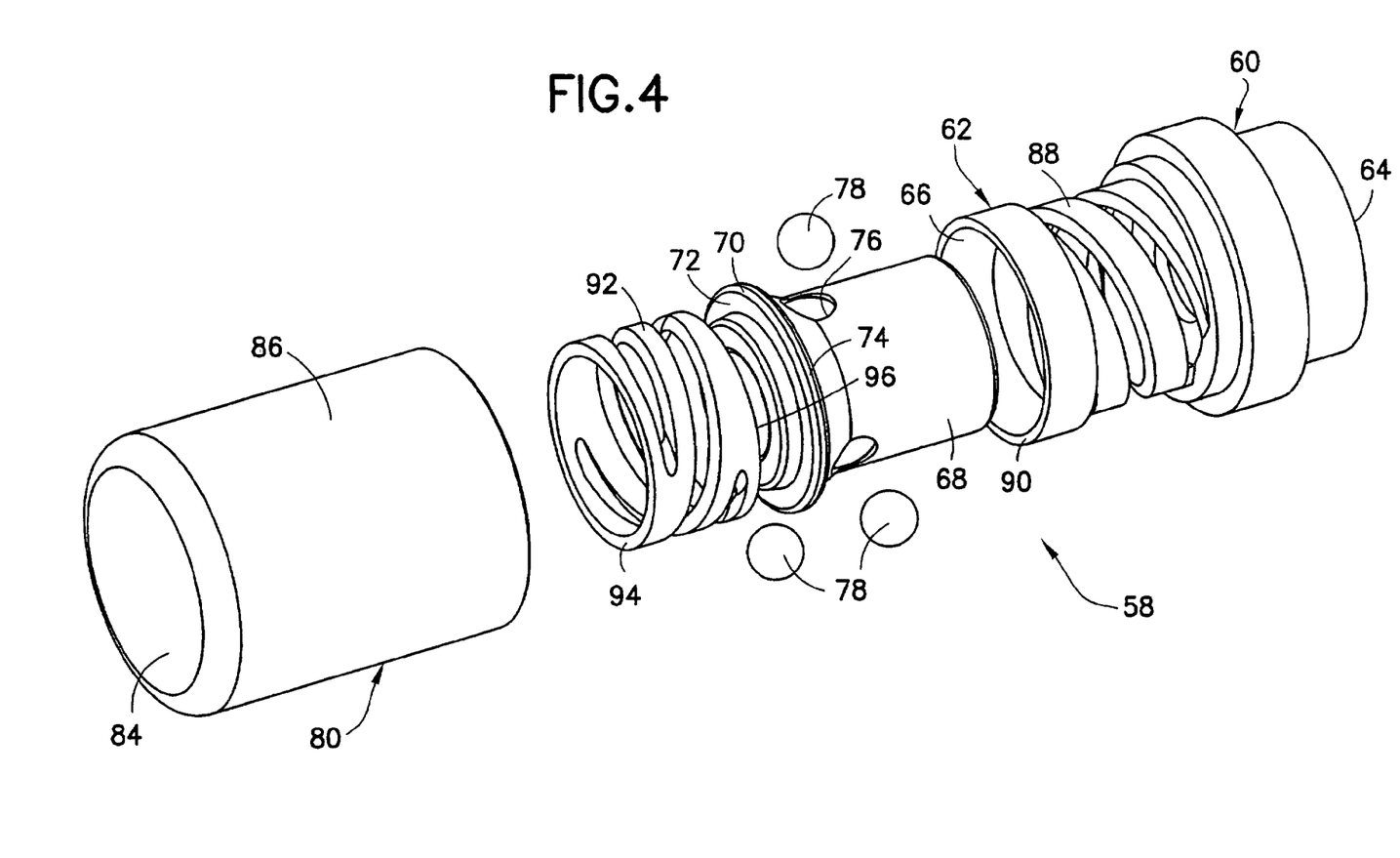
FIG. 4 is an exploded perspective view of the components of the connector system illustrated in FIG. 3.

The connector system 40 used with the pacemaker includes an electrically conductive connector body 44 extending between proximal and distal ends 46, 48 and defining a lead receiving channel 50 having an open end 52 for slidably receiving a connecting lead tip pin 54 of an electrical lead 56. Turning additionally now to FIGS. 3 and 4, a tip assembly 58 is seen being coaxial with the connector body 44 and mounted on the proximal end 46 of the connector body, as by way of a force or interference fit, for slidably engageably receiving the lead tip pin 54. The tip assembly 58 includes an electrically conductive retention mechanism to be described for achieving and maintaining electrical continuity with the lead tip pin 54 and for more firmly engaging the lead tip pin with ever increasing insertion thereof into the lead receiving channel 50.

Figure 5:
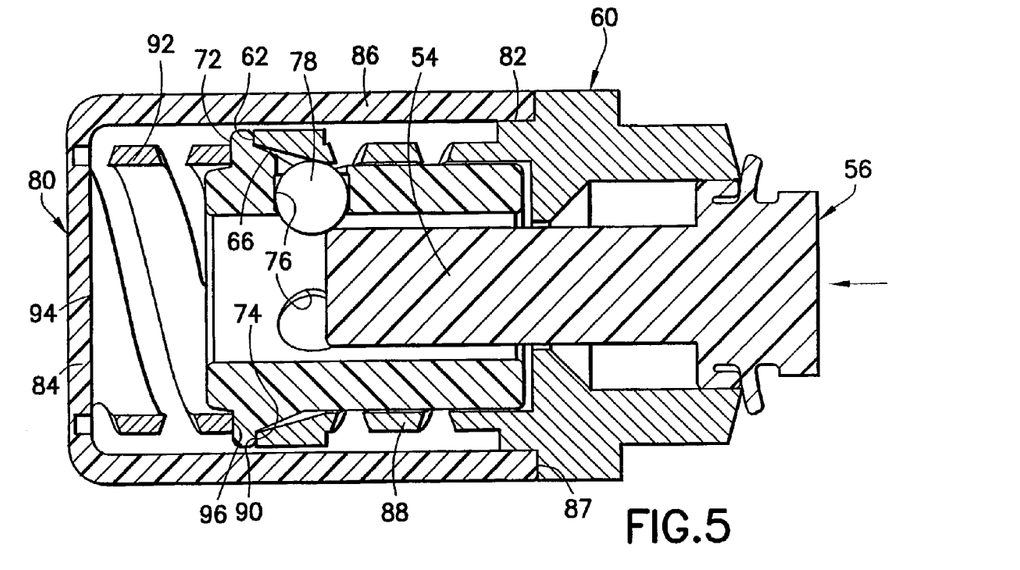
FIG. 5 is a longitudinal cross section view of FIG. 3 illustrating one position of the components.

To this end, the tip assembly 58 has a longitudinal axis which is an extension of the longitudinal axis of the connector system 40 and includes an electrically conductive housing 60 having a proximal end 62 and having a distal end 64 suitably mounted, as by an interference fit, on the proximal end 46 of the connector body 44. The proximal end 62 of the housing 60 is formed with an annular ramp surface 66 (FIGS. 5 and 6) which generally faces the longitudinal axis of the housing and is inclined to flare outwardly toward the proximal end. In another manner of speaking, the annular ramp surface 66 is radially spaced from the longitudinal axis by a distance which increases as the proximal end 62 of the housing 60 is approached.

A tubular carrier 68 is another component of the tip assembly 58 and is coaxial with the housing 60 and with the connector body 44. The tubular carrier 68 includes an annular rib 70 coaxial with the connector body 44 and has proximal and distal annular faces 72, 74 which are most clearly seen in FIGS. 5 and 6. Additionally, the tubular carrier 68 is formed with a plurality of circumferentially spaced apertures 76. A plurality of bearing members 78 are rotatably received in each of the circumferentially spaced apertures 76 so as to be engageable with the lead tip pin 54 and with the annular ramp surface 66 of the housing. The bearing members 78 are preferably balls as illustrated, but other shapes or types of bearing members may be used for the invention.

An end cap 80 overlies the components of the tip assembly 58 just described and is fittingly engageable with the proximal end 62 of the housing 60. More specifically, the housing 60 has an annular recessed shoulder 82 at its proximal end 62. The end cap 80 which is preferably composed of polysulfone or other clear pastic material is cup shaped having a proximal base 84 and a cylindrical side wall 86 projecting away from the base to a distal rim 87 fittingly engaged with the recessed shoulder 82.

At its proximal end 62, the housing 60 is formed with an integral first helical spring 88 having a tip end 90 engageable with the distal face 74 of the annular rib 70. A second helical spring 92 extends between proximal and distal ends 94, 96, respectively, the proximal end being engaged with the proximal base 84 of the end cap 80 and the distal end being engaged with the proximal face 72 of the annular rib 70. The helical spring 92 serves to bias the bearing members 78 into engagement with the annular ramp surface 66 and with the lead tip pin 54.

Figure 6:
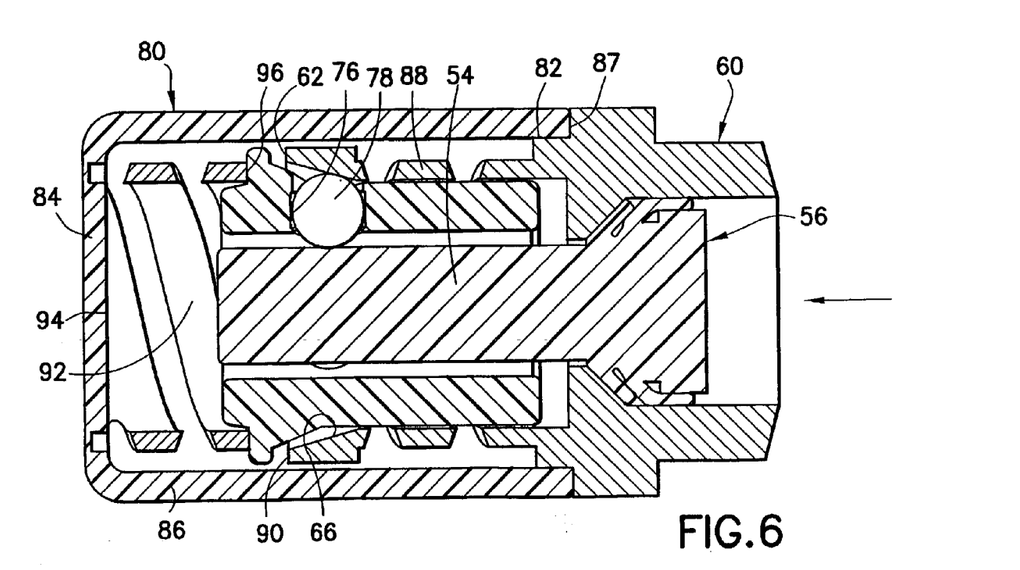
FIG. 6 is a longitudinal cross section view of FIG. 3 illustrating another position of the components.

With this construction, upon insertion of the lead tip pin 54 into the lead receiving channel 50 (FIG. 5), the lead tip pin engages the balls 78, forcing them radially outward from the longitudinal axis of the connector system 40, causing them to advance along the annular ramp surface 66 of the first helical spring 88 thereby causing the tip end 90 to withdraw from engagement with the distal face 74 of the annular rib 70 (FIG. 6). The lead is then engaged by the tubular carrier 68 with a first degree of force.

To remove the lead 56, it is necessary to overcome the forces the bearing members 78 exert on the lead. These forces comprise the normal force and the friction force. As removal tension is applied to the lead, the bearing members start rolling down the ramp surface 66 wedging themselves tighter and tighter between the lead tip pin 54 and the ramp surface, which increases the engagement force exerted by the tubular carrier 68 on the lead 56. When the bearing members cannot move any farther, the extraction force exerted on the lead pulls on the tubular carrier 68 compressing the first helical spring 88. The spring 88 deflects until the tubular carrier engages the inner wall of the metal housing. The force required to deflect the first helical spring 88 is the lead extraction force.

At this instance, the tubular carrier 68 cannot move any farther. The first helical spring 88 is fully compressed. This compression releases some of the load being exerted on the bearing members 78 through the ramp surface 66. This reduces the normal load between the bearing members and the lead tip pin 54. As the pull out force on the lead 56 increases, it becomes greater than the friction force and the lead tip pin 54 starts to slide under the bearing members. This allows the removal of the lead 56 from the connector system 40. Once the lead is removed, the first helical spring 88 relaxes back to its original free state resetting the system for the next lead insertion.

Figure 7:
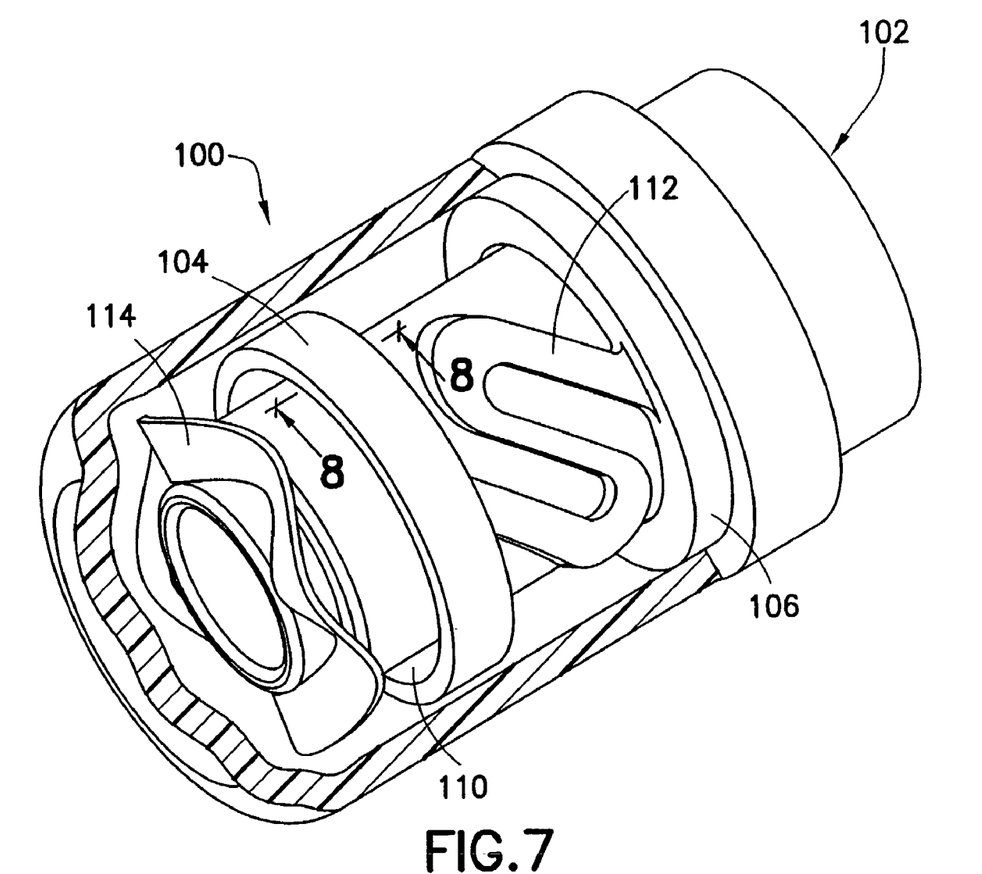
FIG. 7 is a perspective view of a part of a modified connector system embodying the present invention for an implantable medical device.
Figure 8:
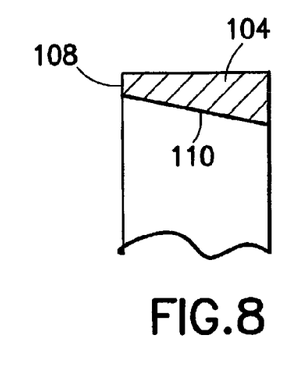
FIG. 8 is a detail cross section view taken generally along line 8—8 in FIG. 7.

Turn now to FIGS. 7 and 8 for another embodiment of the invention. In this instance, a modified connector system includes a modified tip assembly 100 in which a modified housing 102 includes integral distal and proximal longitudinally spaced rings 104, 106, the proximal ring having a proximal annular surface 108 engageable with the distal face 74 of the annular rib 70, as earlier described, and an annular ramp surface 110 generally facing the longitudinal axis of the tip assembly 100.

Turn now to FIGS. 7 and 8 for another embodiment of the invention. In this instance, a modified connector system includes a modified tip assembly 100 in which a modified housing 102 includes integral distal and proximal longitudinally spaced rings 104, 106, the proximal ring having a proximal annular surface 108 engageable with the distal face 74 of the annular rib 70, as earlier described, and an annular ramp surface 110 generally facing the longitudinal axis of the tip assembly 100.

The operation of the connector system utilizing the modified tip assembly 100 is generally similar to that of the connector system 40.

Figure 9:
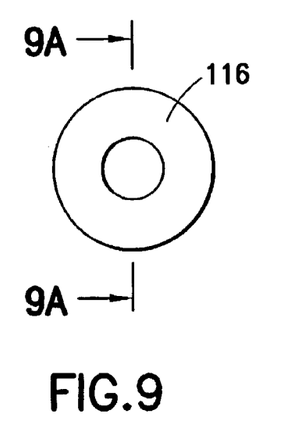
FIG. 9 is an elevation view of a modified component of the modified connector system illustrated in FIG. 8.
Figure 9A:
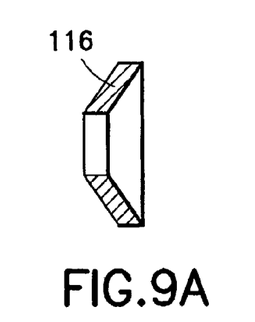
FIG. 9A is a cross section view taken generally along line 9A—9A in FIG. 9.

In another embodiment if the invention, the spring member 114 may be replaced with a spring washer 116 in the form of a Belleville washer as seen in FIGS. 9 and 9A.

Figure 10:
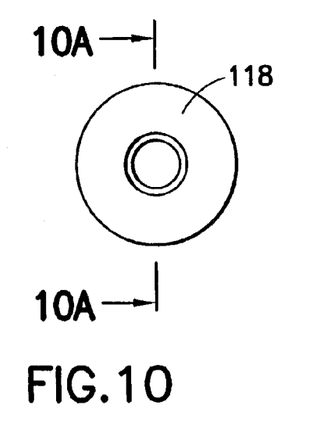
FIG. 10 is an elevation view of a another modified component of the modified connector system illustrated in FIG. 8.
Figure 10A:
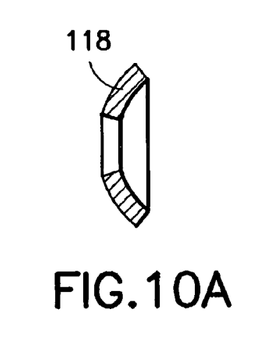
FIG. 10A is a cross-section view taken generally along line 10A—10A in FIG. 10.

In still another embodiment if the invention, the spring member 114 may be replaced with a spring washer 118 in the form of a curved washer as seen in FIGS. 10 and 10A.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A connector system for use with a sealed implantable medical device having a lead receiving channel for slidably receiving a connecting lead tip pin of an electrical lead, the lead receiving channel having an open end for receiving the lead tip pin, the connector system comprising:
   an electrically conductive connector body on the medical device extending between proximal and distal ends and defining the lead receiving channel; and
   a tip assembly connected to the connector body and configured for slidably and engageably receiving the lead tip pin, the tip assembly comprising an electrically conductive retention mechanism for achieving and maintaining electrical continuity with the lead tip pin, wherein at least a portion of the retention mechanism is configured to be displaced during insertion of the lead tip pin into the lead receiving channel to engage the lead tip pin, and wherein at least a portion of the retention mechanism is configured to be displaced during removal of the lead tip pin from the lead receiving channel so as to increase engagement of the lead tip pin;
   wherein the retention mechanism comprises:
      a tubular carrier coaxial with the connector body;
      a plurality of bearing members rotatably mounted on the tubular carrier engageable with the lead tip pin; and
      a resilient member biasing the bearing members into engagement with the lead tip pin.

2. A connector system as set forth in claim 1, wherein the lead tip pin is disposed at a proximal end of the electrical lead.

3. A connector system for use with a sealed implantable medical device having a lead, receiving channel for slidably receiving a connecting lead tip pin of an electrical lead, the lead receiving channel having an open end for receiving the lead tip pin, the connector system comprising:
   an electrically conductive connector body on the medical device extending between proximal and distal ends and defining the lead receiving channel; and
   a tip assembly connected to the connector body and configured for slidably and engageably receiving the lead tip pin, the tip assembly comprising an electrically conductive retention mechanism for achieving and maintaining electrical continuity with the lead tip pin, wherein at least a portion of the retention mechanism is configured to be displaced during insertion of the lead tip pin into the lead receiving channel to engage the lead tip pin, and wherein at least a portion of the retention mechanism is configured to be displaced during removal of the lead tip pin from the lead receiving channel so as to increase engagement of the lead tip pin;
   wherein the tip assembly has a longitudinal axis and comprises:
      an electrically conductive housing having a proximal end and having a distal end mounted on the proximal end of the connector body and comprising an annular ramp surface at the proximal end which generally faces the longitudinal axis and is radially spaced from the longitudinal axis by a distance which increases as the proximal end is approached;
      a tubular carrier coaxial with the housing and with the connector body;
      a plurality of bearing members rotatably mounted on the tubular carrier engageable with the lead tip pin and with the annular ramp surface of the housing; and
      a resilient member biasing the bearing members into engagement with the annular ramp surface and with the lead tip pin.

4. A connector system as set forth in claim 3 comprising an end cap overlying the tip assembly and fittingly engageable with the proximal end of the housing; and
   wherein the tubular carrier comprises an annular rib coaxial with the connector body, the annular rib having proximal and distal annular faces;
   wherein the proximal end of the housing comprises an integral first helical spring having a tip end engageable with the distal face of the annular rib; and
   wherein the resilient member comprises a second helical spring having a proximal end engaged with the end cap and a distal end engaged with the proximal face of the annular rib.

5. A connector system as set forth in claim 4:
   wherein the housing has an annular recessed shoulder at its proximal end; and
   wherein the end cap is cup shaped having a proximal base and a cylindrical side wall projecting away from the base to a distal rim fittingly engaged with the recessed shoulder.

6. A connector system as set forth in claim 4:
   wherein the tubular carrier has a plurality of circumferentially spaced apertures;
   wherein the bearing members include balls rotatably received in each of the circumferentially spaced apertures;
   wherein the housing has an annular recessed shoulder at its proximal end; and wherein the end cap is cup shaped having a proximal base and a cylindrical side wall projecting away from the base to a distal rim fittingly engaged with the recessed shoulder;

whereby with insertion of the lead tip pin into the lead receiving channel, the lead tip pin engages the balls, forcing them radially outward from the longitudinal axis, causing them to advance along the annular ramp surface of the first helical spring thereby causing the tip end of the first helical spring to withdraw from engagement with the distal face of the annular rib.

7. A connector system as set forth in claim 3 comprising an end cap overlying the tip assembly and fittingly engageable with the proximal end of the housing; and wherein the tubular carrier comprises an annular rib coaxial with the connector body, the annular rib having proximal and distal annular faces;

wherein the housing comprises:

integral distal and proximal longitudinally spaced rings, the proximal ring having a proximal annular surface engageable with the distal face of the annular rib and the annular ramp surface generally facing the longitudinal axis; and a pair of diametrically opposed s-shaped springs extending between the distal ring and the proximal ring; and wherein the resilient member comprises a second spring member interposed between and engaged with the end cap and with the proximal face of the annular rib.

8. A connector system as set forth in claim 7:

wherein the housing has an annular recessed shoulder at its proximal end; and wherein the end cap is cup shaped having a proximal base and a cylindrical side wall projecting away from the base to a distal rim fittingly engaged with the recessed shoulder.

9. A connector system as set forth in claim 7:

wherein the tubular carrier has a plurality of circumferentially spaced apertures;

wherein the bearing members include balls rotatably received in each of the circumferentially spaced apertures;

wherein the housing has an annular recessed shoulder at its proximal end; and wherein the end cap is cup shaped having a proximal base and a cylindrical side wall projecting away from the base to a distal rim fittingly engaged with the recessed shoulder;

whereby with insertion of the lead tip pin into the lead receiving channel, the lead tip pin engages the balls, forcing them radially outward from the longitudinal axis, causing them to advance along the annular ramp surface of the proximal ring thereby causing the proximal annular surface of the proximal ring to withdraw from engagement with the distal face of the annular rib.

10. A connector system as set forth in claim 7, wherein the second spring comprises a curved washer.

11. A connector system as set forth in claim 7, wherein the second spring comprises a wave washer.

12. A connector system as set forth in claim 7, wherein the second spring comprises a Belleville washer.

13. A connector system as set forth in claim 3, wherein the lead tip pin is disposed at a proximal end of the electrical lead.

14. A connector system for use with an implantable medical device, the connector system being adapted for receiving a connecting lead tip pin of an electrical lead, the connector system comprising:

an electrically conductive connector body on the medical device extending between proximal and distal ends and defining a lead receiving channel; and a tip assembly connected to the connector body and configured for receiving the lead tip pin, the tip assembly comprising an electrically conductive retention mechanism in electrical contact with the connector body, wherein the retention mechanism comprises a displaceable subassembly that is displaced upon insertion of the lead tip pin to engage the lead tip pin with a first degree of force, wherein the subassembly is displaced during withdrawal of the lead tip pin so that the retention mechanism engages the lead tip pin with a second degree of force that is greater than the first degree of force, and wherein the displaceable subassembly comprises a plurality of rotatable bearing members to engage with the lead tip pin.

15. A connector system as set forth in claim 14, wherein the lead tip pin is disposed at a proximal end of the electrical lead.

* * * * *